United States Patent [19]

Dostalek et al.

[11] Patent Number: 5,767,329
[45] Date of Patent: Jun. 16, 1998

[54] PURITY OF 1,6-HEXANEDIOL

[75] Inventors: Roman Dostalek, Römerberg; Rolf Fischer, Heidelberg; Wolfgang Harder, Weinheim; Axel Paul, Lampertheim; Rolf Pinkos, Bad Dürkheim, all of Germany

[73] Assignee: BASF Aktiengesellschaft, Ludwigshafen, Germany

[21] Appl. No.: 860,604

[22] PCT Filed: Jan. 4, 1996

[86] PCT No.: PCT/EP96/00023

§ 371 Date: Jul. 1, 1997

§ 102(e) Date: Jul. 1, 1997

[87] PCT Pub. No.: WO96/20909

PCT Pub. Date: Jul. 11, 1996

[30] Foreign Application Priority Data

Jan. 5, 1995 [DE] Germany ............... 195 00 236.9

[51] Int. Cl.$^6$ .................. C07C 31/18; C07C 27/26; C07C 29/74
[52] U.S. Cl. .................. 568/852; 568/868; 568/872
[58] Field of Search ................... 568/868, 852, 568/872

[56] References Cited

U.S. PATENT DOCUMENTS

| 3,524,892 | 8/1970 | Horlenko | 568/864 |
| 3,933,930 | 1/1976 | Dougherty | 568/864 |
| 5,659,092 | 8/1997 | McNabb | 568/868 |

OTHER PUBLICATIONS

WPIDS abstract of EP 790266, 1997.
WPIDS abstract of JP 09100335, 1997.
Chemical Abstract 102:132936, abstract of DE 3320260, 1984.
WPIDS abstract of DE 2060548, 1979.

Primary Examiner—Alan L. Rotman
Assistant Examiner—D. Margaret M. Mach
Attorney, Agent, or Firm—Keil & Weinkauf

[57] ABSTRACT

Impurities are separated from aqueous solutions of 1,6-hexanediol or 1,6-hexanediol precursors, such as adipic and 6-hydroxycaproic acid, by a process which comprises adding at least one carboxylic acid to a solution (a) of 1,6-hexanediol and subjecting this solution (a) or a solution (b) containing carboxylic acid(s) as precursor(s) of 1,6-hexanediol to a heat treatment at temperatures above room temperature in the absence of hydrogen.

10 Claims, No Drawings

PURITY OF 1,6-HEXANEDIOL

This application is a 371 of PCT/GP96/00023, filed Jan. 4, 1996.

The present invention relates to a process for the preparation of 1,6-hexanediol of high purity. The present invention relates in particular to a process which permits the separation of cyclic hexanediols, such as 1,4-dihydroxycyclohexane, and cyclic hydroxyketones, such as 4-hydroxycyclohexanone, from solutions which contain 1,6-hexanediol or 1,6-hexanediol precursors, such as adipic acid, 6-hydroxycaproic acid and/or other stripper acids (stripper acids are understood very generally as meaning mixtures of mono- and dicarboxylic acids).

It is known that 1,6-hexanediol, a diol widely used as a monomer component for polyesters, can be produced industrially by hydrogenation of adipic acid and/or 6-hydroxycaproic acid and subsequent distillation of the discharged hydrogenation mixture [Ullmanns Enzyklopädie der technischen Chemie, 4th Edition, Vol. 7, page 228 et seq. (1974)].

Aqueous solutions consisting of adipic acid, 6-hydroxycaproic acid and/or many other mono- and dicarboxylic acids, ie. stripper acids, are formed, for example, as a coupling product in the oxidation of cyclohexane to cyclohexanol/cyclohexanone mixtures and in the subsequent working up of the oxidation product. Such solutions contain from 10 to 50% by weight of adipic acid and 6-hydroxycaproic acid and about 0.1–3% by weight of cyclohexanediols and hydroxycyclohexanones. These cyclic diols are relatively stable to hydrogenation and therefore are substantially retained even after the hydrogenation of the abovementioned acids to 1,6-hexanediol, whereas the hydroxycyclohexanones are hydrogenated to cyclohexanediols. These cyclohexanediols are very difficult to separate from 1,6-hexanediol, even by distillation.

A possible method for removing these cyclic diols from the abovementioned solutions, for example solutions containing adipic acid, is described in U.S. Pat. No. 3,933,930. According to this, the oxidation of cyclohexane is followed by a catalytic prehydrogenation step, so that 1,4-dihydroxycyclohexane (formed in the oxidation of cyclohexane) is converted into cyclohexanol, cyclohexane and/or cyclohexene without substantial hydrogenation of, for example, adipic acid and 6-hydroxy-hexanoic acid. However, this prehydrogenation step requires the use of a hydrogenation catalyst which differs from the hydrogenation catalyst for the actual reduction, ie. for the reduction of the adipic acid and of the 6-hydroxyhexanoic acid to 1,6-hexanediol. The prehydrogenation is carried out in the presence of molecular hydrogen under high pressures (300 atm), making the total reaction even more expensive.

DE-A-20 60 548 describes a process for the purification of 1,6-hexanediol which contains small amounts of other diols by crystallization. The hexanediol purity thus achieved is stated there as 99.8%. Although this process gives very pure 1,6-hexanediol, it is disadvantageous in that it requires very high capital costs.

It is an object of the present invention to provide a process by means of which undesirable cyclic hexanediols which are difficult to separate off can be separated selectively, without expensive apparatus and relatively cheaply from solutions which either already contain 1,6-hexanediol or its precursors.

We have found that this object is achieved, according to the invention, by a simplified process as defined in claim 1. A preferred process is one in which (a) solutions of 1,6-hexanediol to which carboxylic acids have first been added or
(b) solutions of the precursors of 1,6-hexanediol (eg. of adipic acid) are heated to 300° C. without the addition of a hydrogenation catalyst and without hydrogen. This makes it possible to remove the undesirable cyclic hexanediols from solutions (a) and (b) without a hydrogenation catalyst and hydrogen being required, as in U.S. Pat. No. 3,933,930. Accordingly, the cost of the apparatus required and consequently the costs for the preparation of purified 1,6-hexanediol are reduced.

Further preferred features or embodiments of the invention are evident from the following description and from the Examples.

As stated above, aqueous wash solutions—ie. stripper acids—which contain in particular adipic acid and 6-hydroxycaproic acid (altogether from about 10 to 80% by weight) in addition to small amounts of cyclic diols are obtained in the catalytic oxidation of cyclohexane to cyclohexanol/cyclohexanone mixtures. If these wash solutions are subjected to a catalytic hydrogenation and subsequent distillation of the hydrogenation product, 1,6-hexanediol which contains cyclic diols is obtained. These are essentially the cis- and trans-isomers of 1,2-cyclohexanediol, 1,3-cyclohexanediol and 1,4-cyclohexanediol.

By heating the abovementioned solutions (a) and (b), the troublesome cyclohexanediols or hydroxycyclohexanones are degraded to a large extent without the 1,6-hexanediol or its precursors being destroyed. The extent to which the cyclohexanediols or hydroxycyclohexanones are destroyed depends essentially on the temperature and on the duration of the thermal treatment. The preferred temperature is 130°–300° C., the range from 180° to 260° C. being particularly preferred. The reaction time, ie. the duration of the thermal treatment, also influences the extent of degradation of the undesirable cyclohexanediols. Usual reaction times are from a few minutes to several hours. Preferred reaction times are from 10 minutes to 20 hours, particularly preferably 0.3–10 hours.

The weight ratio of added carboxylic acid in solution (a) or the acids (precursors of 1,6-hexanediol) of solution (b) on the one hand to the cyclohexanediols to be eliminated on the other hand is not critical. However, the ratio should be at least 1:1, preferably greater than or equal to 5:1, based on the particular weight, an excess of the carboxylic acids in (a) or in (b) relative to the cyclohexanediols being preferred since such an excess leads to an increase in the reaction rate.

The reaction of the cyclohexanediols in the novel process takes place preferably in aqueous systems. Accordingly, the weight ratio of water to cyclohexanediols also influences the course of the reaction and the reaction rate. According to the present invention, the weight ratio of water to cyclohexanediols should be at least 5:1, higher weight ratios, eg. from 15:1 to 30:1 or even higher ratios, being preferred. In particular, starting mixtures which contain up to 5% by weight, based on the starting mixture, ie. including water, of cyclohexanediols are heated according to the invention.

In the simplest case, the reaction is carried out by heating solutions (a) or (b) to the abovementioned temperatures (130°–300° C.) in a pressure-resistant reactor while stirring. The residence time of the particular solution in the pressure-resistant reactor determines the degree of conversion, ie. the increase in concentration or removal, of the cyclohexanediols. Instead of this batchwise procedure, however, the continuous procedure in which solution (a) or (b) is passed into a heated stirred reactor or into a reaction tube and is removed continuously from the hot reaction zone while maintaining the desired residence time is also suitable.

Suitable carboxylic acids which can be added to the 1,6-hexanediol for the preparation of solution (a) or which may be present in the mixture of the precursors (solution (b)) are all aliphatic $C_1$–$C_{20}$-monocarboxylic acids, all $C_2$–$C_{18}$-dicarboxylic acids, and aromatic and araliphatic as well as halogen-containing carboxylic acids. These preferably include the monocarboxylic acids acetic, propionic, butyric, valeric and caproic acid as well as the dicarboxylic acids oxalic, malonic, succinic, glutaric, adipic and 6-hydroxycaproic acid. Particularly preferred carboxylic acids are adipic and 6-hydroxycaproic acid.

For the novel separation of cyclohexanediols from the abovmentioned solutions (a) and (b), it is as a rule not necessary to use a catalyst. However, a catalyst may be advantageous when particularly short residence times are desired. In such a case, the novel reaction can be carried out in the presence of acidic catalysts, such as mineral acids, sulfonic acids, heteropoly acids, strongly acidic ion exchangers, zeolites, aluminosilicates, $SiO_2$, $Al_2O_3$, $TiO_2$ and/or $ZrO_2$. Acidic oxides, such as $SiO_2$, $Al_2O_3$ or $TiO_2$, or mixtures of these oxides are preferred. In order to increase the acid strength of the oxides, they may be doped with sulfate or phosphate groups, the amount by weight being from 0.5 to 10% (based on the total weight).

If the thermally treated solution was solution (a), the hydrogenation of, for example, adipic and 6-hydroxycaproic acid has already been carried out under the conditions known from the prior art (cf. for example German Published Application DAS 1,235,879). The reaction of the troublesome cyclohexanediols in the discharged aqueous hydrogenation mixture is therefore then carried out, after the reduction of the acids to 1,6-hexanediol and after the addition of the abovementioned carboxylic acids with preparation of solution (a), by heating to high temperatures (130°–300° C.) without it being necessary to add a hydrogenation catalyst and hydrogen.

Alternatively, the novel thermal treatment can, however, also be applied directly to the precursors of 1,6-hexanediol, ie. solution (b). The thermal treatment according to the present invention is then followed by the known hydrogenation by means of a hydrogenation catalyst (as described, for example, in German Published Application DAS 1,235,879). The discharged hydrogenation mixtures obtained in this manner can then be separated by distillation, 1,6-hexanediol with a substantially reduced content of cyclohexanediols being obtained.

The Examples described below not only illustrate the novel process but also show that this process is extremely suitable for obtaining a substantially purer solution of 1,6-hexanediol by conversion of contaminating cyclohexanediols.

EXAMPLE 1

150 ml of dicarboxylic acid solution (54% by weight of water, 16.5% by weight of adipic acid, 17.8% by weight of 6-hydroxycaproic acid and 1.8% by weight of cyclohexanediols, the remainder to 100% by weight comprising further mono- and dicarboxylic acids) are heated in a 300 ml pressure-resistant reactor for 5 hours at 250° C. (autogenous pressure 50 bar=$5\times10^6$ Pa) while stirring. The water content can be determined by the Karl Fischer method, the carboxylic acid content by HPLC and the cyclohexanediol content, after trifluoroacetylation of the dicarboxylic acid solution with trifluoroacetic anhydride, by gas chromatography.

After the end of the experiment, the reaction mixture is cooled to room temperature and analyzed again:

| | |
|---|---|
| Water content: | 55% by weight |
| Adipic acid content: | 16.2% by weight |
| 6-Hydroxycaproic acid content: | 18.1% by weight |
| Cyclohexanediol content: | 0.19% by weight |
| Further mono- and dicarboxylic acids: | Remainder to 100% by weight |

EXAMPLE 2

A dicarboxylic acid solution (having a cyclohexanediol content of 1.6% by weight and containing 17% by weight of adipic acid and 17.3% by weight of 6-hydroxycaproic acid) is heated to 230° C. similarly to Example 1. After 5 and 20 hours in each case, samples are taken and their cyclohexanediol content is investigated:

| | |
|---|---|
| Cyclohexanediol content after experimental time of 5 hours: | 0.27% by weight |
| Cyclohexanediol content after experimental time of 20 hours: | 0.08% by weight |

EXAMPLE 3

The dicarboxylic acid solution from Example 1 is fed continuously at a rate of 40 ml/h (corresponding to an average residence time of 1.75 hours) through a reaction tube maintained at 230° C. and having a volume of 70 ml. About 10 l of the dicarboxylic acid solution pretreated in this manner are fed continuously at a rate of 130 g/h into a 300 ml hydrogenation reactor heated to 240° C. and containing 200 ml of a cobalt catalyst. The hydrogen pressure is 250 bar ($2.5\times10^7$ Pa). The average residence time of the dicarboxylic acid solution in the hydrogenation reactor is 2–3 hours. A gas chromatographic analysis of the discharged hydrogenation mixture gives:

| | |
|---|---|
| 1,6-Hexanediol content: | 31.3% by weight |
| Cyclohexanediol content: | 0.7% by weight |

COMPARATIVE EXAMPLE

The dicarboxylic acid solution from Example 3 is not preheated but is continuously hydrogenated while maintaining the same reaction parameters, similarly to Example 3. GC analysis of the discharged hydrogenation mixture gives the following result:

| | |
|---|---|
| 1,6-Hexanediol content: | 30.4% by weight |
| Cyclohexanediol content: | 1.74% by weight |

EXAMPLE 4

1.6 g of hexanoic acid are added to 150 g of a mixture of 69% by weight of water, 30% by weight of 1,6-hexanediol and 1% by weight of 1,4-cyclohexanediol and the stirred mixture is heated at 250° C. for 5 hours. The gas chromatographic analysis of the discharged reaction mixture after the end of the experiment gives a 1,4-cyclohexanediol content of 0.49% by weight.

EXAMPLE 5

A dicarboxylic acid solution (55% by weight of water, 17% by is weight of adipic acid, 15% by weight of 6-hydroxycaproic acid and 2% by weight of cyclohexanediols, the remainder to 100% by weight comprising further mono- and dicarboxylic acids) is fed continuously at a rate of 1200 ml/h through a reaction tube filled with 400 ml of $SiO_2$ extrudates (4 mm diameter) and then passed through a 2.5 l hydrogenation reactor which is heated to 230° C. and contains 2.4 ml of the Co catalyst stated in Example 3. The hydrogen pressure is 260 bar. The temperature in the $SiO_2$-filled reaction tube is initially 25° C. The analysis of the discharged hydrogenation mixture gives:

| 1,6-Hexanediol content: | 23% by weight |
|---|---|
| Cyclohexanediol content: | 2.3% by weight |

1,6-Hexanediol content: 23% by weight Cyclohexanediol content: 2.3% by weight

After an experimental time of 3 days, the temperature in the $SiO_2$-filled reaction tube is increased to 220° C. The analysis of the discharged hydrogenation mixture gives:

| 1,6-Hexanediol content: | 23% by weight |
|---|---|
| Cyclohexanediol content: | 1.2% by weight |

We claim:

1. A process for separating impurities from aqueous solutions of 1,6-hexanediol or 1,6-hexanediol precursors selected from adipic and 6-hydroxycaproic acid, which comprises adding at least one carboxylic acid to a solution (a) of 1,6-hexanediol and subjecting this solution (a) or a solution (b) containing said 1,6-hexane diol precusors to a heat treatment at temperatures above room temperature in the absence of hydrogen.

2. A process as claimed in claim 1, wherein the added carboxylic acid is one or more of $C_2$–$C_{20}$-monocarboxylic acid(s), $C_2$–$C_{18}$-dicarboxylic acid or a mixture thereof, said mono- and dicarboxylic acid may optionally contain at least one member selected from the group consisting of aromatic radical, cycloaliphatic radical, heterocyclic radical or halogen atom.

3. A process as claimed in claim 1, wherein the added carboxylic acid is adipic acid, 6-hydroxycaproic acid or a mixture thereof.

4. A process as claimed in any of claim 1, wherein the temperature during the heat treatment is 130°–300° C.

5. A process as claimed in claim 1, wherein solution (a) or (b) is heated over a period of from 10 minutes to 20 hours.

6. A process as claimed in claim 1, wherein the solution is heated in the presence of an acidic catalyst.

7. A process as claimed in claim 1, wherein, after the heat treatment, solution (b) is subjected to a conventional hydrogenation so that the precursors are converted into 1,6-hexanediol.

8. A process as claimed in claim 1, wherein the impurity to be separated off is one or more cyclohexanediol.

9. A process as claimed in claim 8, wherein the weight ratio of the carboxylic acid to the cyclohexanediol to be removed is greater than or equal to 1:1.

10. A process as claimed in claim 8, wherein the weight ratio of water to the cyclohexanediol to be removed is greater than or equal to 5:1.

* * * * *